(12) United States Patent
Choi et al.

(10) Patent No.: US 11,202,597 B2
(45) Date of Patent: Dec. 21, 2021

(54) ELECTROCARDIOGRAM MEASUREMENT DEVICE FOR VEHICLE, SYSTEM INCLUDING THE SAME, AND METHOD THEREFOR

(71) Applicants: Hyundai Motor Company, Seoul (KR); Kia Motors Corporation, Seoul (KR)

(72) Inventors: Yoon Jong Choi, Daejeon (KR); Hyun Wook Jun, Seoul (KR); Yeong Joon Gil, Busan (KR); Min Yong Shin, Gyeonggi-do (KR); Soo Hwan Kim, Gyeonggi-do (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 461 days.

(21) Appl. No.: 15/830,408

(22) Filed: Dec. 4, 2017

(65) Prior Publication Data

US 2019/0082993 A1    Mar. 21, 2019

(30) Foreign Application Priority Data

Sep. 19, 2017   (KR) .................... 10-2017-0120581

(51) Int. Cl.
*A61B 5/282*   (2021.01)
*A61B 5/18*   (2006.01)
(Continued)

(52) U.S. Cl.
CPC ................ *A61B 5/282* (2021.01); *A61B 5/18* (2013.01); *A61B 5/276* (2021.01); *A61B 5/316* (2021.01);
(Continued)

(58) Field of Classification Search
CPC . A61B 5/04012; A61B 5/0245; A61B 5/0432; A61B 5/18; A61B 5/6893;
(Continued)

(56) References Cited

U.S. PATENT DOCUMENTS

| 8,086,300 B2 | 12/2011 | Herlerkson |
| 2008/0243013 A1 | 10/2008 | Yanai et al. |

(Continued)

FOREIGN PATENT DOCUMENTS

| JP | 2009-142575 A | 7/2009 |
| JP | 2011-024902 A | 2/2011 |

(Continued)

*Primary Examiner* — Tammie K Marlen
(74) *Attorney, Agent, or Firm* — Mintz Levin Cohn Ferris Glovsky and Popeo, P.C.; Peter F. Corless

(57) ABSTRACT

An electrocardiogram (ECG) measurement device for a vehicle is provided. The ECG measurement device includes an impedance compensator that corresponds to an electrode in contact with a body of a driver and configured to compensate an impedance of each of electrode signals received from the electrode. An electrode selector sequentially selects the electrode signals in response to receiving the electrode signals from the electrode. A differential amplifier differentially amplifies the electrode signals. In particular, each electrode signal has the compensated impedance. Additionally, a signal quality evaluator evaluates quality of an ECG signal output from the differential amplifier and a compensation controller then adjusts an impedance compensation value of each of the impedance compensators as a result of evaluating the quality of the ECG signal.

11 Claims, 12 Drawing Sheets

(51) Int. Cl.
- *A61B 5/00* (2006.01)
- *A61B 5/276* (2021.01)
- *A61B 5/316* (2021.01)
- *A61B 5/333* (2021.01)
- *A61B 5/0245* (2006.01)
- *A61B 5/322* (2021.01)

(52) U.S. Cl.
CPC ............ *A61B 5/333* (2021.01); *A61B 5/6893* (2013.01); *A61B 5/7221* (2013.01); *A61B 5/0006* (2013.01); *A61B 5/0245* (2013.01); *A61B 5/322* (2021.01); *A61B 5/7203* (2013.01)

(58) Field of Classification Search
CPC ....... A61B 5/7221; A61B 5/282; A61B 5/276; A61B 5/333; A61B 5/316; A61B 5/322; A61B 5/0006; A61B 5/7203
See application file for complete search history.

(56) References Cited

U.S. PATENT DOCUMENTS

| | | |
|---|---|---|
| 2010/0007413 A1 | 1/2010 | Herleikson |
| 2015/0327815 A1 | 11/2015 | Hwang |

FOREIGN PATENT DOCUMENTS

| | | |
|---|---|---|
| JP | 2012-040241 A | 3/2012 |
| JP | 2014-124438 A | 7/2014 |
| KR | 10-1421698 B1 | 8/2014 |
| KR | 10-1519960 B1 | 5/2015 |
| KR | 10-1579517 B1 | 12/2015 |
| KR | 10-2016-0043417 A | 4/2016 |
| WO | 2008-056309 A2 | 5/2008 |

ELECTROCARDIOGRAM MEASUREMENT DEVICE FOR VEHICLE, SYSTEM INCLUDING THE SAME, AND METHOD THEREFOR

CROSS-REFERENCE TO RELATED APPLICATION

This application is based on and claims the benefit of priority to Korean Patent Application No. 10-2017-0120581, filed on Sep. 19, 2017, the disclosure of which is incorporated herein in its entirety by reference.

TECHNICAL FIELD

The present disclosure relates to an electrocardiogram (ECG) measurement device for a vehicle, a system including the same, and a method therefor, and more particularly, relates to technologies for measuring an ECG based on a plurality of multiple electrodes of a driver while a vehicle is driven.

BACKGROUND

Generally, patients suffering from chronic hypertension maintain their health with adherence to proper medical management. Typically, patients suffering from chronic hypertension also measure their hypertension. When a numeric value of the hypertension suddenly changes immediate action is required. In particular, when a significant change in blood sugar or blood pressure of a driver occurs during operation of the vehicle, this increases the risk of a potential vehicle collision.

Accordingly, an electrocardiograph may be used for monitoring blood pressure of a driver. The electrocardiograph refers to a device which measures a minimal difference in activity potential (e.g., a voltage of 1 mV), generated from heart muscles when a heart is beating, using electrodes attached to biometric surfaces and records and displays a change curve over time. A curve obtained at this time may refer to an electrocardiogram (ECG). An electrical waveform (an ECG) due to a heartbeat indicated by an ECG is analyzed to diagnose ischemic heart diseases, such as arrhythmia, angina, and myocardial infarction (a heart attack), hypertrophy and dilatation of atriums and ventricles, and the like. A clinical electrocardiograph may simultaneously perform measurement in 1 to 12 channels based on a channel and may perform electrocardiography by connecting 5 to 10 lead lines to a periphery of a heart, a wrist, and an ankle using electrodes.

However, there are significant limitations to measuring 12 channels and measuring an ECG by connecting a wrist and an ankle to electrodes to measure the ECG during operation of a vehicle, and many methods for measuring the ECG use electrodes of a steering wheel and a seat. However, when an electrode is limited to a steering wheel and both hands are not in contact with electrodes of the steering wheel, measuring an ECG may be difficult. Further, a method for measuring an ECG in a seat, requires many electrodes to enhance a differential amplification rate and the measurement may be inaccurate and obscured by clothing.

The above information disclosed in this section is merely for enhancement of understanding of the background of the disclosure and therefore it may contain information that does not form the prior art that is already known in this country to a person of ordinary skill in the art.

SUMMARY

The present disclosure has been made to solve the above-mentioned problems occurring in the prior art while advantages achieved by the prior art are maintained intact. An aspect of the present disclosure provides an ECG measurement device for a vehicle for measuring an ECG in various situations of a driver based on a plurality of multiple electrodes while a vehicle is driven, a system including the same, and a method therefor. Another aspect of the present disclosure provides an ECG measurement device for a vehicle for compensating an impedance of an N channel in multiple channels for overcoming shortcomings of a 2-channel common mode rejection ratio (CMRR), a system including the same, and a method therefor.

According to an aspect of the present disclosure, an electrocardiogram (ECG) measurement device for a vehicle may include impedance compensator configured to correspond to an electrode which is in contact with a body of a driver and configured to compensate an impedance of a plurality electrode signals received from the electrode, an electrode selector configured to sequentially select the plurality of electrode signals when receiving the plurality of electrode signals from the electrode, a differential amplifier configured to differentially amplify the plurality of electrode signals, each of which has the compensated impedance; a signal quality evaluator configured to evaluate quality of an ECG signal output from the differential amplifier and a compensation controller configured to adjust an impedance compensation value of the impedance compensator as a result of evaluating the quality of the ECG signal.

In an exemplary embodiment, the signal quality evaluator may be configured to detect strength and a noise component of the ECG signal and evaluate the quality of the ECG signal using the detected strength and noise component of the ECG signal. In an exemplary embodiment, the electrode may be installed in a steering wheel, a gear change lever, a window button, a door armrest, a radio volume adjuster, an armrest, a handle, a horn, a turn signal level, a glove compartment, or a seat belt. The ECG measurement device for the vehicle may further include a contact sensor configured to detect that the body of the driver is in contact with the electrode and transmit active signals to the impedance compensator based thereon, when the body of the driver is in contact with the electrode.

The electrode selector when receiving electrode signals output from electrodes that recognizes contact with the driver by the contact sensor may sequentially select the received electrode signals as a first input signal and a second input signal of the differential amplifier.

The compensation controller may be configured to adjust an impedance compensation value of an electrode signal selected as the first input signal of the differential amplifier or an impedance compensation value of an electrode signal selected as the second input signal of the differential amplifier on an independent basis as a result of evaluating the quality of the ECG signal. In addition, the compensation controller may be configured to adjust the impedance compensation value based on vehicle information and the result of evaluating the quality of the ECG signal. The compensation controller may then be configured to terminate the adjustment of the impedance compensation value when the quality of the ECG signal is greater than a predetermined threshold.

According to another aspect of the present disclosure, an ECG measurement system for a vehicle may include an ECG measurement device for the vehicle configured to output an ECG signal using a plurality of electrode signals generated when a body of a driver is in contact with an electrode(s), from the electrode in contact with the body of the driver, evaluate quality of the ECG signal, and adjust impedance compensation of the plurality of electrode signals and an ECG recorder configured to store the ECG signal and the evaluation result of the quality of the ECG signal.

In an exemplary embodiment, the ECG measurement device for the vehicle may include an impedance compensator configured to correspond to the electrode and compensate an impedance of the plurality of electrode signals received from the electrode, an electrode selector configured to sequentially select the at least one of the plurality of electrode signals when receiving the plurality of electrode signals from the electrode, a differential amplifier configured to differentially amplify the plurality of electrode signals, each of which has the compensated impedance, a signal quality evaluator configured to evaluate quality of an ECG signal output from the differential amplifier, and a compensation controller configured to adjust an impedance compensation value of the impedance compensator based on the ECG signal quality evaluation result.

In addition, the signal quality evaluator may be configured to detect strength and a noise component of the ECG signal and evaluate the quality of the ECG signal based on the detected strength and noise component of the ECG signal. In an exemplary embodiment, the electrode may be disposed in of a steering wheel, a gear change lever, a window button, a door armrest, a radio volume adjuster, an armrest, a handle, a horn, a turn signal level, a glove compartment, or a seat belt. In an exemplary embodiment, the ECG measurement device for the vehicle may further include a contact sensor configured to detect that the body of the driver is in contact with the electrode and transmit active signals to the impedance compensator, when the body of the driver is in contact with the electrode.

In an exemplary embodiment, the electrode selector may be configured to sequentially select the received electrode signals as a first input signal and a second input signal of the differential amplifier when receiving electrode signals output from electrodes with which contact of the driver is recognized by the contact sensor. The compensation controller may be configured to adjust an impedance compensation value of an electrode signal selected as the first input signal of the differential amplifier or an impedance compensation value of an electrode signal selected as the second input signal of the differential amplifier on an independent basis as a result of evaluating the quality of the ECG signal. In an exemplary embodiment, the ECG measurement device for the vehicle may further include an interface configured to display the ECG signal.

According to another aspect of the present disclosure, an ECG measurement method for a vehicle may include when recognizing contact of a body of a driver with a first electrode among an electrode in contact with the body of the driver, outputting a first electrode signal from the first electrode, when recognizing contact of a body of the driver with a second electrode, outputting a second electrode signal from the second electrode may be output, an ECG signal by differentially amplifying the first electrode signal and the second electrode signal, evaluating quality of the ECG signal and adjusting impedance compensation of the first electrode signal or the second electrode signal as a result of evaluating the quality of the ECG signal.

In an exemplary embodiment, the method may further include, storing the ECG signal in an ECG recorder when the quality of the ECG signal is greater than or equal to a threshold. In an exemplary embodiment, the evaluating of the quality of the ECG signal may include detecting strength and a noise component of the ECG signal and evaluating the quality of the ECG signal based on the detected strength and noise component of the ECG signal.

In an exemplary embodiment, the adjusting of the impedance compensation may include adjusting an impedance compensation value of the first electrode signal or the second electrode signal on an independent basis as a result of evaluating the quality of the ECG signal. In an exemplary embodiment, the adjusting of the impedance compensation may include adjusting an impedance compensation value of the first electrode signal or the second electrode signal on an independent basis using the result of evaluating the quality of the ECG signal and vehicle information.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Figure 1:
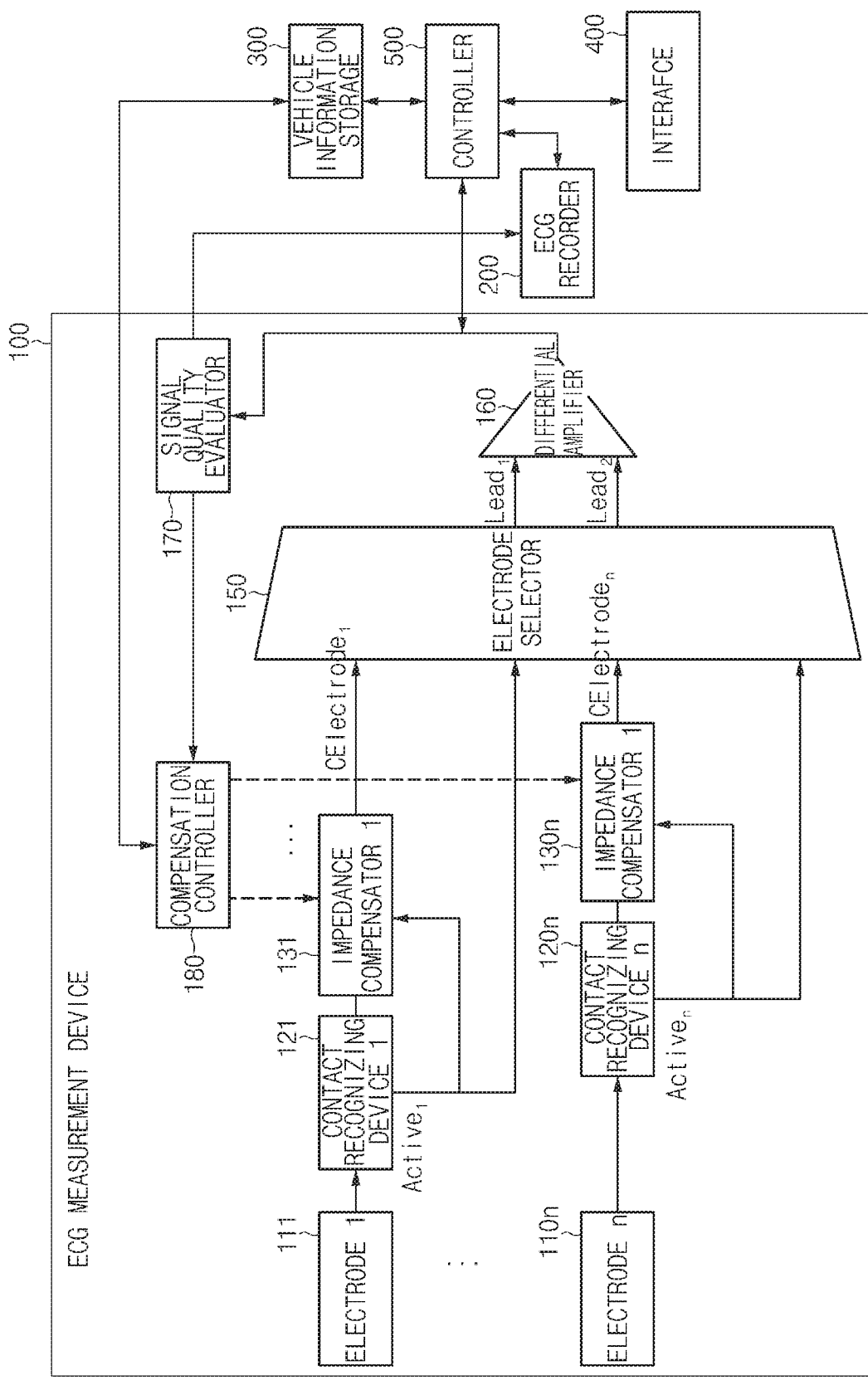
FIG. 1 is an exemplary block diagram illustrating a configuration of an ECG measurement system for a vehicle according to an exemplary embodiment of the present disclosure.

Hereinafter, exemplary embodiments of the present disclosure will be described in detail with reference to the accompanying drawings. In adding reference denotations to elements of each drawing, although the same elements are displayed on a different drawing, it should be noted that the same elements have the same denotations. In addition, in describing an embodiment of the present disclosure, if it is determined that a detailed description of related well-known configurations or functions blurs the gist of an embodiment of the present disclosure, it will be omitted.

In describing elements of exemplary embodiments of the present disclosure, the terms 1st, 2nd, first, second, A, B, (a), (b), and the like may be used herein. These terms are only used to distinguish one element from another element, but do not limit the corresponding elements irrespective of the nature, turn, or order of the corresponding elements. Unless otherwise defined, all terms used herein, including technical or scientific terms, have the same meanings as those generally understood by those skilled in the art to which the present disclosure pertains. Such terms as those defined in a generally used dictionary are to be interpreted as having meanings equal to the contextual meanings in the relevant field of art, and are not to be interpreted as having ideal or excessively formal meanings unless clearly defined as having such in the present application.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, the term "and/or" includes any and all combinations of one or more of the associated listed items. For example, in order to make the description of the present disclosure clear, unrelated parts are not shown and, the thicknesses of layers and regions are exaggerated for clarity. Further, when it is stated that a layer is "on" another layer or substrate, the layer may be directly on another layer or substrate or a third layer may be disposed therebetween.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although exemplary embodiment is described as using a plurality of units to perform the exemplary process, it is understood that the exemplary processes may also be performed by one or plurality of modules. Additionally, it is understood that the term controller/control unit refers to a hardware device that includes a memory and a processor. The memory is configured to store the modules and the processor is specifically configured to execute said modules to perform one or more processes which are described further below.

Furthermore, control logic of the present disclosure may be embodied as non-transitory computer readable media on a computer readable medium containing executable program instructions executed by a processor, controller/control unit or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

It is understood that the term "vehicle" or "vehicular" or other similar term as used herein is inclusive of motor vehicle in general such as passenger automobiles including sports utility vehicles (SUV), buses, trucks, various commercial vehicles, watercraft including a variety of boats, ships, aircraft, and the like and includes hybrid vehicles, electric vehicles, combustion, plug-in hybrid electric vehicles, hydrogen-powered vehicles and other alternative fuel vehicles (e.g. fuels derived from resources other than petroleum).

Figure 2:
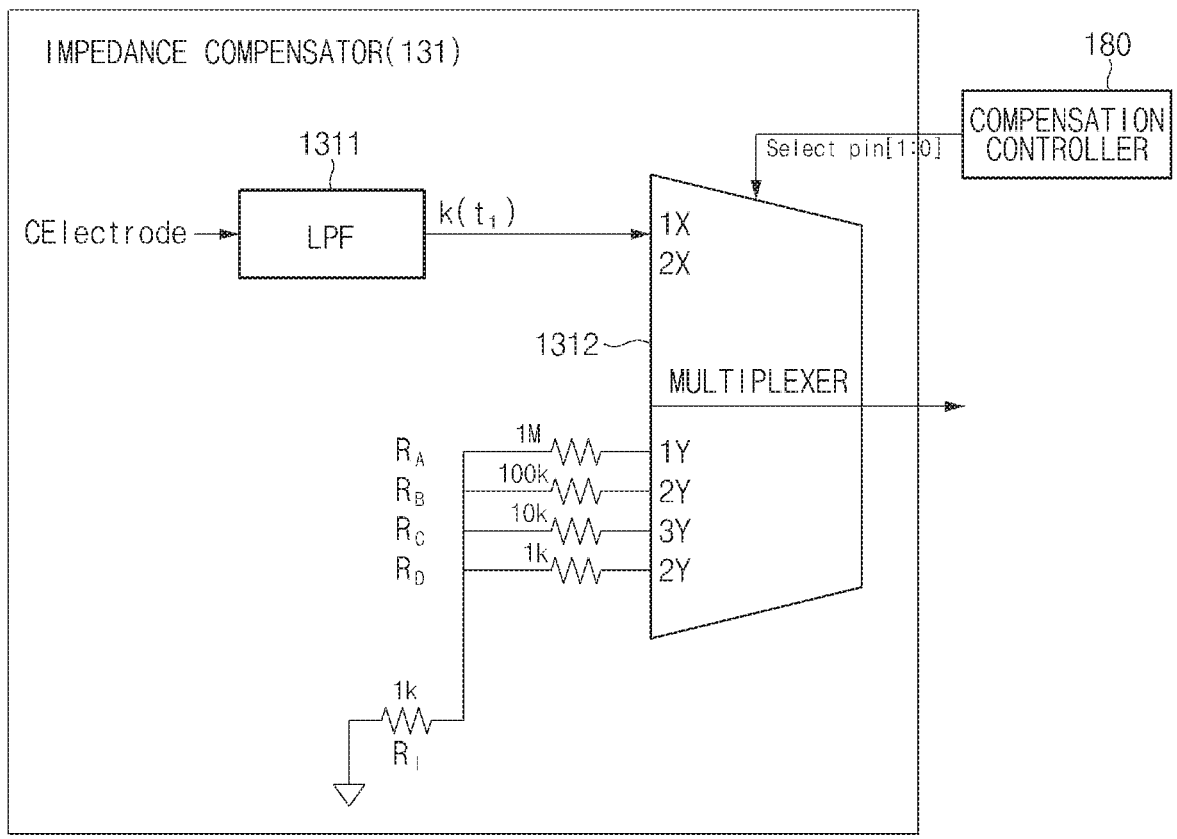
FIG. 2 is an exemplary detailed circuit diagram illustrating a configuration of an impedance compensator according to an exemplary embodiment of the present disclosure.

Hereinafter, a description will be given in detail of exemplary embodiments of the present disclosure with reference to FIGS. 1 to 10. FIG. 1 is an exemplary block diagram illustrating a configuration of an ECG measurement system for a vehicle according to an exemplary embodiment of the present disclosure. FIG. 2 is an exemplary detailed circuit diagram illustrating a configuration of an impedance compensator according to an exemplary embodiment of the present disclosure. The ECG measurement system for the vehicle according to an exemplary embodiment of the present disclosure may include an ECG measurement device 100 for the vehicle, an ECG recorder 200, a vehicle information storage 300, an interface 400, and a controller 500. The ECG measurement device 100 may be configured to output an ECG signal using a plurality of (e.g., at least one or more) electrode signals generated when in contact with a body of a driver, from an (e.g., at least one or more) electrodes which are in contact with the body of the driver and may evaluate quality of the ECG signal, thus adjusting impedance compensation of the plurality of electrode signals.

In particular, the ECG measurement device 100 may include a plurality of electrodes 111 to 110n, a plurality of contact sensor s121 to 120n, a plurality of impedance comparators 131 to 130n, an electrode selector 150, a differential amplifier 160, a signal quality evaluator 170, and a compensation controller 180. When the body of the driver is in contact with the plurality of electrodes 111 to 110n, each of the plurality of electrodes 111 to 110n may be configured to output an electrode signal. In other words, the plurality of electrodes 111 to 110n may be disposed in a steering wheel in the vehicle, a gear change lever, a window button, a door armrest, a radio volume adjuster, an armrest, a handle, a horn, a turn signal level, a glove compartment, a seat belt, or the like.

Figure 6:
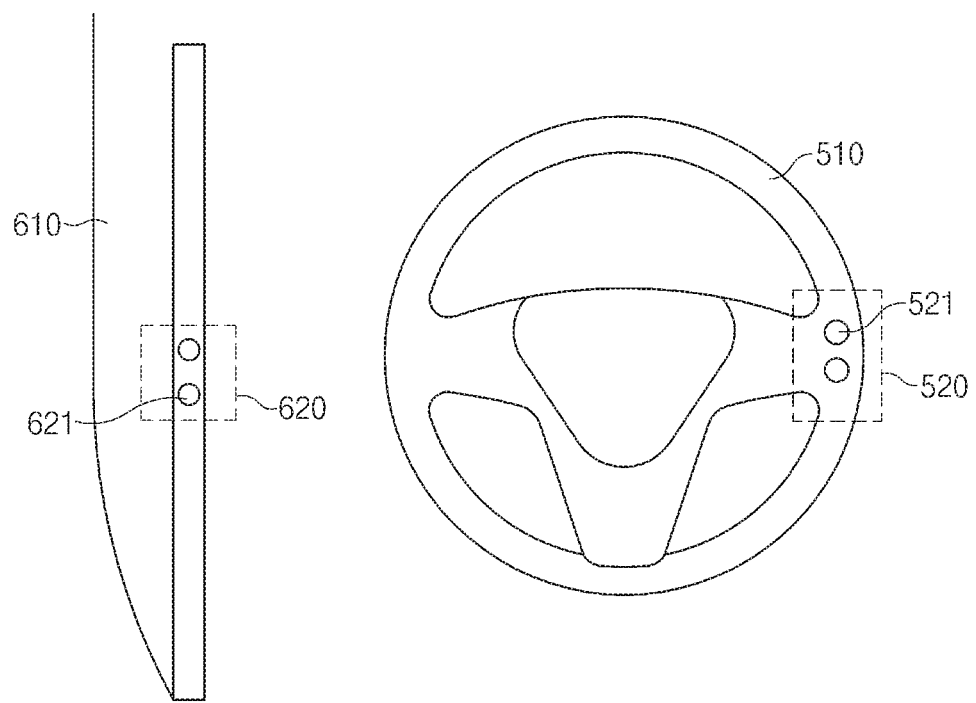
FIG. 6 is an exemplary drawing illustrating an example in which a plurality of electrodes for measuring an ECG are installed in a vehicle, according to an exemplary embodiment of the present disclosure.
Figure 7:
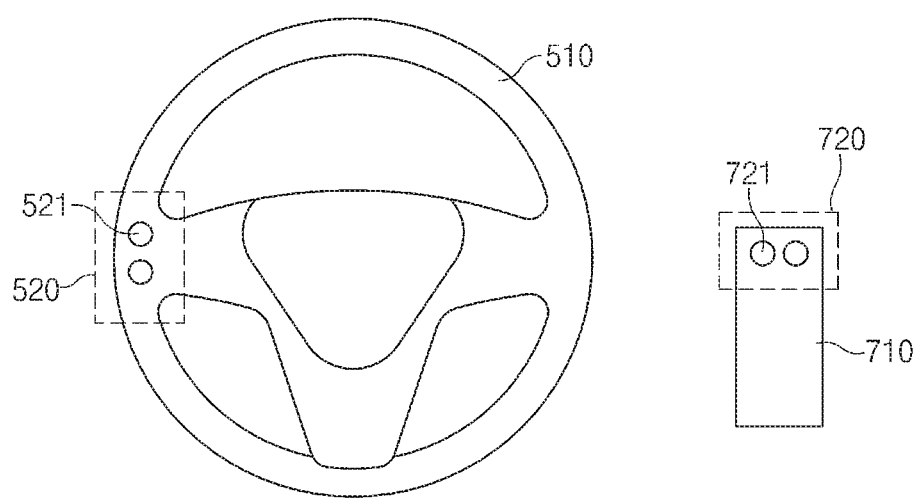
FIG. 7 is an exemplary drawing illustrating an example in which a plurality of electrodes for measuring an ECG are installed in a vehicle, according to another exemplary embodiment of the present disclosure.

FIG. 6 is an exemplary drawing illustrating an example in which a plurality of electrodes for measuring an ECG are disposed in a vehicle, according to an exemplary embodiment of the present disclosure. FIG. 7 is an exemplary drawing illustrating an example in which a plurality of electrodes for measuring an ECG are disposed in a vehicle, according to another exemplary embodiment of the present disclosure. Referring to FIG. 6, when a driver pushes a window button 620 with his or her first hand (e.g., left hand or right hand) to open a window 610 and holds a steering wheel 510 with his or her second hand (e.g., right hand or left hand), electrode signals may be output from an electrode 621 mounted on the window button 620 and an electrode 521 mounted on the steering wheel 510 and his or her ECG may be measured from a differential amplification value of the two electrode signals.

Referring to FIG. 7, when the first hand of the driver is in contact with the electrode 521 mounted on the steering wheel 510 and when the driver's second hand is in contact with an electrode 721 mounted on a gearshift lever 710 for a gear operation, the driver's ECG may be measured by a differential amplification signal of electrode signals output from the electrodes 521 and 721. Each of a plurality of contact sensor 121 to 120n of FIG. 1 may determine whether a body of the driver is in contact with each of a plurality of electrodes 111 to 110n. When the body of the driver is in contact with each of the plurality of electrodes 111 to 110n, the plurality of contact sensor 121 to 120n may be configured to output a plurality of active signals Active1 to Activen to a plurality of impedance compensators 131 to 130n and an electrode selector 150.

Each of the plurality of impedance compensators 131 to 130n may be configured to compensate an impedance of an electrode signal based on a previously stored impedance compensation value. In other words, since each of the plurality of electrodes 111 to 110n has impedance, generated by each electrode location, a wire connected with each electrode, and the like, for each electrode, a noise may occur due to the impedance. Thus, each of the plurality of impedance compensators 131 to 130n may be configured to compensate an impedance of an electrode signal based on a previously stored impedance compensation value. Further, when receiving an active signal, each of the plurality of impedance compensators 131 to 130n may be activated. An impedance compensation value may be configured to be adjusted by a compensation controller 180 of FIG. 1. Referring to FIG. 2, each of the plurality of impedance compensators 131 to 130n, for example, an impedance compensator 131 may include a low pass filter (LPF) 1311 and a multiplexer 1312. When receiving an electrode signal, the LPF 1311 may be configured to perform filtering.

The multiplexer 1312 may include a plurality of resistors RA, RB, RC, RD, and RI. A plurality of filters may be included based on a plurality of ratios of resistor RI to resistors RA, RB, RC, and RD. A compensation control value adjusted by the compensation controller 180 may refer to selecting one of the plurality of ratios. In other words, an amplification rate may be determined based on the ratio of resistor RI to each of resistors RA, RB, RC, and RD. For example, when the compensation controller 180 selects the ratio of resistor RI to resistor RA, an electrode signal may be amplified at the selected ratio of resistor RI to resistor RA. In FIG. 2, an exemplary embodiment may be exemplified as four resistors RA, RB, RC, and RD are included in the multiplexer 1312. However, exemplary embodiments are not limited thereto. For example, the multiplexer 1312 may be implemented to have N resistors and select N amplification ratios. Further, in FIG. 2, it is not shown that an active signal of FIG. 1 is provided to the impedance compensator 131. However, when receiving an active signal from the contact recognizing device 121, the impedance compensator 131 may be activated. Each of a plurality of calculation units may be configured to add a signal output from each of the plurality of impedance compensators 131 to 130n, having impedance compensated to an electrode signal output from each of the plurality of contact sensor 121 to 120n and may provide the added signal to an electrode selector 150 of FIG. 1.

The electrode selector 150 may be configured to select a first electrode signal Lead1 and a second electrode signal Lead2 among electrode signals CElectrode1 to CElectroden, each of which has the compensated impedance as inputs of a differential amplifier 160 of FIG. 1. In particular, when a plurality of electrode signals are simultaneously provided, the electrode selector 150 may be configured to select the plurality of provided the electrode signals in an order where the electrode signals are input.

The differential amplifier 160 may be configured to output an ECG signal by amplifying a difference value between the first electrode signal Lead1 and the second electrode signal Lead2. A signal quality evaluator 170 of FIG. 1 may be configured to evaluate quality of the ECG signal output from the differential amplifier 160. In other words, the signal quality evaluator 170 may be configured to detect strength and a noise component of the ECG signal and may evaluate the quality of the ECG signal using the detected strength and noise component of the ECG signal. When the quality of the ECG signal is greater than or equal to a predetermined threshold, the signal quality evaluator 170 may be configured to transmit the ECG signal to an ECG recorder 200 of FIG. 1 to store the ECG signal. When the quality of the ECG signal is less than the predetermined threshold, the signal quality evaluator 170 may be configured to transmit the ECG signal to a compensation controller 180 of FIG. 1 to compensate the threshold. The predetermined threshold may include that SNR(Signal to Noise Ratio) is −3 db.

Figure 8A:
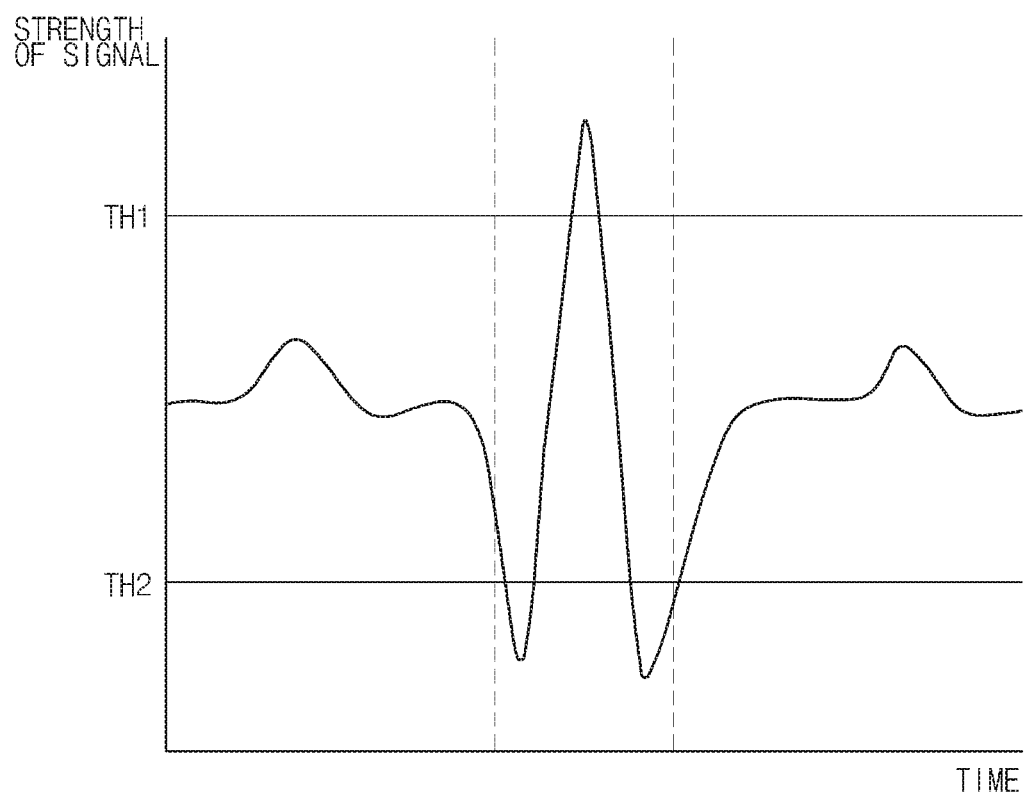
FIG. 8A is an exemplary drawing illustrating a graph indicating that a level of an ECG signal is greater than or equal to a threshold, according to an exemplary embodiment of the present disclosure.
Figure 8B:
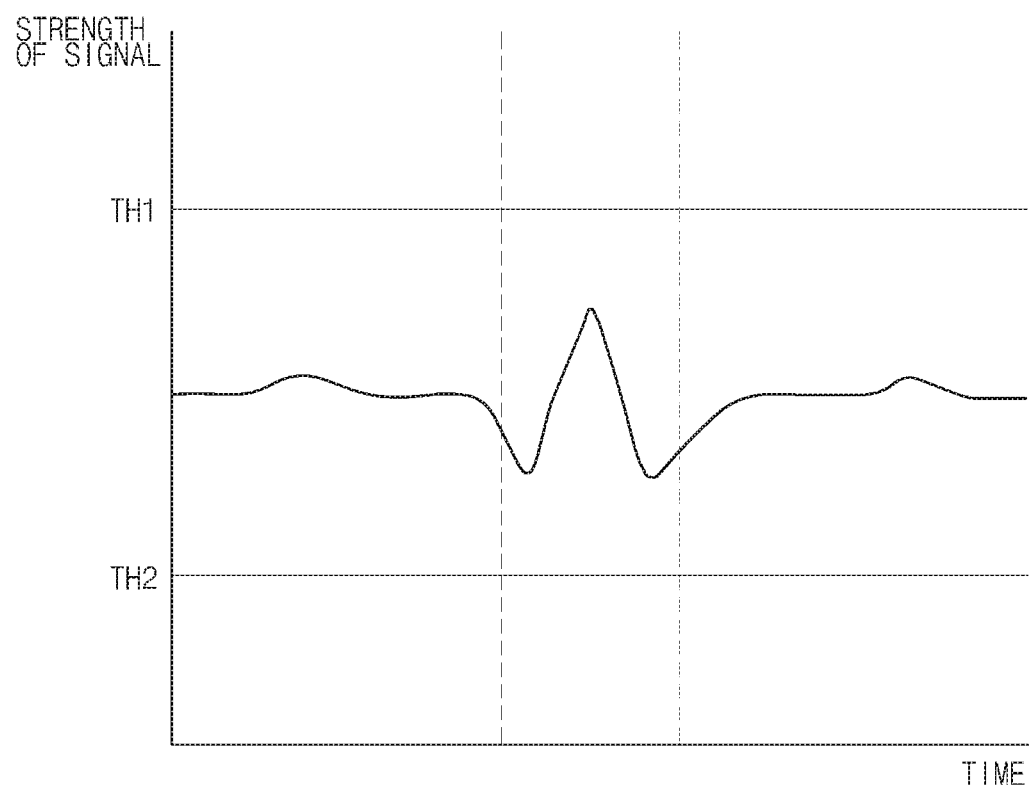
FIG. 8B is an exemplary drawing illustrating a graph indicating that a level of an ECG signal is less than a threshold, according to an exemplary embodiment of the present disclosure.

FIG. 8A is an exemplary drawing illustrating a graph indicating that a level of an ECG signal may be greater than or equal to a threshold, according to an exemplary embodiment of the present disclosure. FIG. 8B is an exemplary drawing illustrating a graph indicating that a level of an ECG signal may be less than a threshold, according to an exemplary embodiment of the present disclosure. Referring to FIG. 8A, the strength of a signal may be greater than thresholds TH1 and TH2 in a constant interval. In particular, a signal quality evaluator 170 of FIG. 1 may be configured to determine that a signal of a sufficient level is obtained and may be configured to transmit the signal to an ECG recorder 200 of FIG. 1. Further, referring to FIG. 8B, when strength of a signal is less than thresholds TH1 and TH2 in a constant interval and is insufficient, the signal quality evaluator 170 may be configured to transmit the signal to the compensation controller 180 for compensation.

Figure 9A:
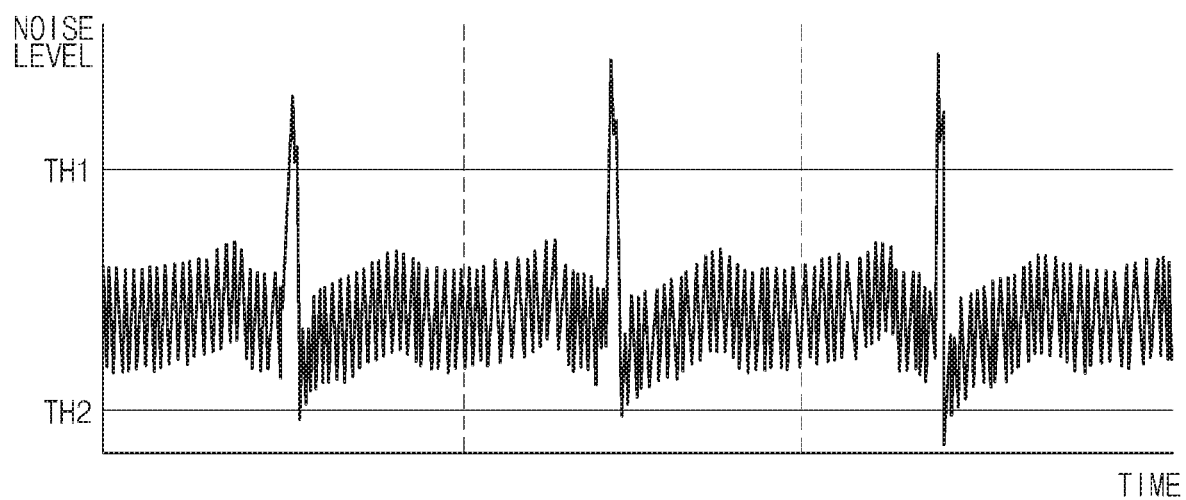
FIG. 9A is an exemplary drawing illustrating a graph indicating that a noise of an ECG signal is high, according to an exemplary embodiment of the present disclosure.
Figure 9B:
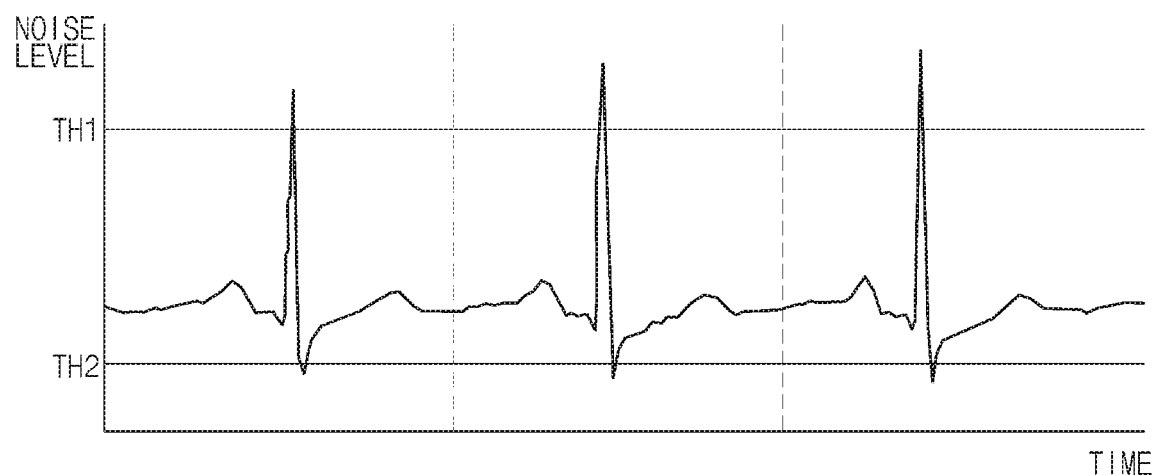
FIG. 9B is an exemplary drawing illustrating a graph indicating that a noise of an ECG signal is low, according to an exemplary embodiment of the present disclosure.

FIG. 9A is an exemplary drawing illustrating a graph indicating that a noise of an ECG signal is high, according to an exemplary embodiment of the present disclosure. FIG. 9B is an exemplary drawing illustrating a graph indicating that a noise of an ECG signal is low, according to an exemplary embodiment of the present disclosure. A signal quality evaluator 170 of FIG. 1 may be configured to calculate a signal to noise ratio (SNR) on a beat-by-beat basis and may be configured to determine that a noise is high when the noise is greater than a threshold. Further, when analyzing a noise power of a constant value or greater to a reference signal through power spectrum analysis, the signal quality evaluator 170 may be configured to determine that a noise is high. Further, the signal quality evaluator 170 may be configured to analyze a noise through differential amplification with the reference signal and may be configured to determine that a noise is elevated when a level of a remaining signal is greater than a threshold. The signal quality evaluator 170 may be configured to determine a noise using various normal methods other than the above-mentioned method.

Referring to FIG. 9A, when strength of an ECG signal is greater than a threshold and when a noise is detected, the signal quality evaluator 170 may be configured to transmit an ECG signal, a noise signal of which is detected, to a compensation controller 180 of FIG. 1 to compensate an impedance of the ECG signal. Referring to FIG. 9B, when the strength of the ECG signal is greater than the threshold and when a noise is not detected, the signal quality evaluator 170 may be configured to determine that quality is good and may be configured to transmit the ECG signal to the ECG recorder 200.

The compensation controller 180 may be configured to adjust an impedance compensation value of each of at least one or more impedance compensators 131 to 130n of FIG. 1 as a result of evaluating the quality of the ECG signal. The compensation controller 180 may be configured to adjust a level and a direction of an impedance compensation value as a result of evaluating the quality of the ECG signal. In other words, the compensation controller 180 may be configured to adjust an impedance compensation value of an electrode signal selected as a first input signal of a differential amplifier 160 of FIG. 1 or an impedance compensation value of an electrode signal selected as a second input signal of the differential amplifier 160 on an independent basis.

In particular, the compensation controller 180 may be configured to adjust an impedance compensation value using vehicle information stored in a vehicle information storage 300 of FIG. 1 and the result of evaluating the quality of the ECG signal. For example, assuming that a noise is excessive at a vehicle speed of 300 km/h through an experimental value, when a vehicle is currently 300 km/h, the compensation controller 180 may be configured to determine that a noise component is excessive and may greatly adjust an impedance compensation value. When the quality of the ECG signal is greater than or equal to a threshold, the compensation controller 180 may be configured to terminate the adjustment of the impedance compensation value.

The ECG recorder 200 may be configured to store an ECG signal transmitted from the signal quality evaluator 170. In particular, the ECG signal may include a result of analyzing an ECG. The ECG recorder 200 may store vehicle information, such as global positioning system (GPS) information, a vehicle speed, a temperature, humidity, or the like, together with personal information of a driver, weather, a time, or the like. An ECG signal (including a heart rate) recorded in the ECG recorder 200 may be displayed on an interface 400 of FIG. 1 to enable a driver to verify the ECG signal. The ECG measurement device 100 of FIG. 1 may be configured to monitor a state of a recorded ECG and may provide a notification to the driver. Alternatively, when determining that an ECG is in an unstable state using a recorded ECG state and vehicle information such as GPS information, a speed, a temperature, and humidity, the ECG measurement device 100 may allow a vehicle to enter an autonomous driving mode or a notification function mode of informing a hospital of the unstable state.

The vehicle information storage 300 may be configured to store a current driving environment (e.g., GPS information, a speed, weather, or the like) of a vehicle, an indoor environment (e.g., a temperature, humidity, or the like), body information (e.g., height, weight, age, gender, or the like) and may provide such information to the compensation controller 180. The interface 400 may display a result of analyzing a biometric signal to inform a driver of a vehicle of the result and may allow the driver to adjust a setting.

A controller 500 of FIG. 1 may be configured to adjust an operation of each of all elements of an ECG measurement system. When the driver rides in the vehicle, the controller 500 may be configured to recognize the driver based on driver information stored in the vehicle information storage 300. Further, the controller 500 may be configured to analyze information, including an ECG and a heart rate, from an ECG signal stored in the ECG recorder 200 and may display the analyzed information on the interface 400. Alternatively, the controller 500 may be configured to adjust the vehicle to enter an autonomous driving mode or a hospital notification function mode based on an ECG state of the driver. Further, the controller 500 may be configured to interwork with the compensation controller 180 using basic body information of the driver to preset an impedance compensation value.

An exemplary embodiment of the present disclosure may increase convenience of the driver by less invasively measuring an ECG, when a driver is in contact with various locations while driving a vehicle without being in contact with a limited specific location in which an electrode is installed, based on a plurality of multiple electrodes installed in a steering wheel, a seat, a gear change lever, a window button, a center fascia, and the like, in the vehicle, in various ways, under a driving environment of the vehicle. Further, the exemplary embodiment of the present disclosure may remove a noise that occurs in various vehicles as well as a common mode noise generated from a body of a driver by sequentially inputting electronic signals although the electronic signals are input for two or more channels without measuring an ECG signal for two channels and adjusting impedance compensation of an electrode signal using the result of evaluating the quality of an ECG signal and vehicle information.

Figure 3:
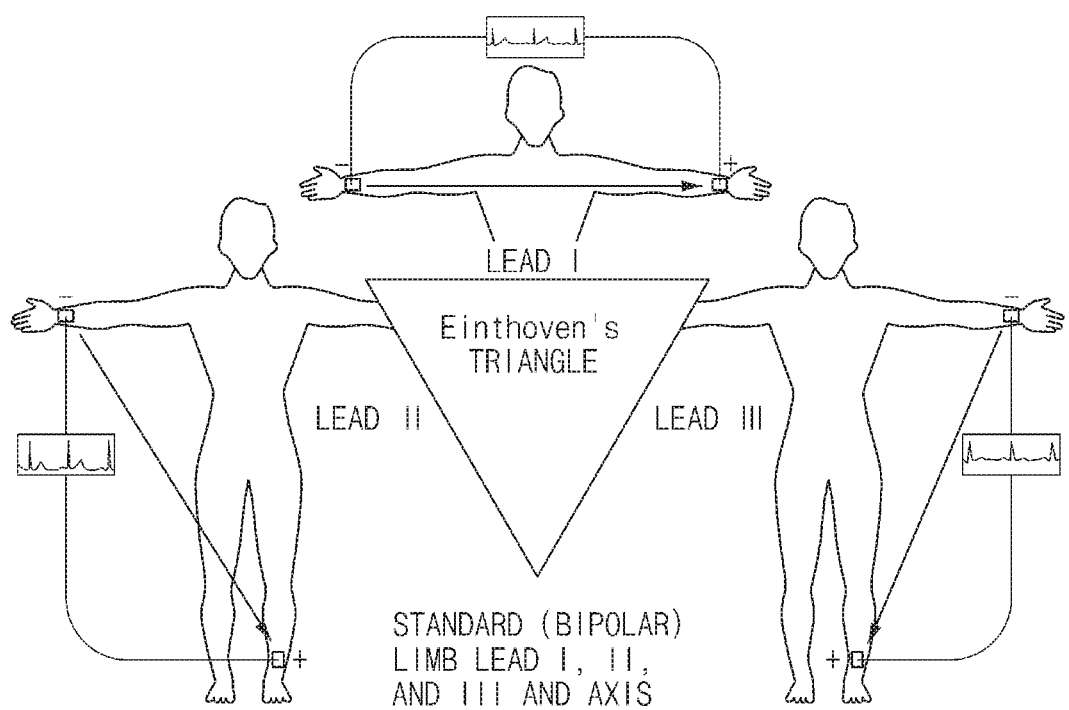
FIG. 3 is an exemplary drawing illustrating an ECG lead method according to an exemplary embodiment of the present disclosure.

FIG. 3 is an exemplary drawing illustrating an ECG lead method according to an exemplary embodiment of the present disclosure. Referring to FIG. 3, an exemplary embodiment of the present disclosure may use a standard bipolar lead scheme for recording a potential difference between two portions of a body of a driver and may select lead I among leads I, II, and III. In other words, the exemplary embodiment of the present disclosure may measure an electric potential difference between both hands of the driver in a lead I scheme. It may be necessary for an electrode which may measure an electric potential of each of a first or second hand of the driver to measure an ECG in the lead I scheme. An exemplary embodiment of the present disclosure may be configured to measure an ECG although the first or second hand of the driver are disposed at various positions, by installing a plurality of electrodes in various positions in a vehicle.

In an exemplary embodiment having electrodes installed in a steering wheel, a change gear, a radio volume adjuster, a window, a driver's seat door armrest, an ECG of the driver may be more accurately measured in various driving situations. For example, when a driver grips the steering wheel with the driver's one hand and touches a gear change lever with the other hand to shift gears when he or she drives a vehicle while holding the steering wheel with two hands, when he or she holds the steering wheel with the driver's one hand and adjusts a radio volume with the other hand, when he or she holds the steering wheel with the driver's one hand and adjusts the window with the other hand using a window button, and when he or she holds the steering wheel and is held on a driver's seat door armrest with the other hand. In other words, exemplary embodiments are not limited to the above-mentioned exemplary embodiments. As there are more electrodes applicable in a vehicle, additional combinations of exemplary embodiments may occur.

Figure 4:
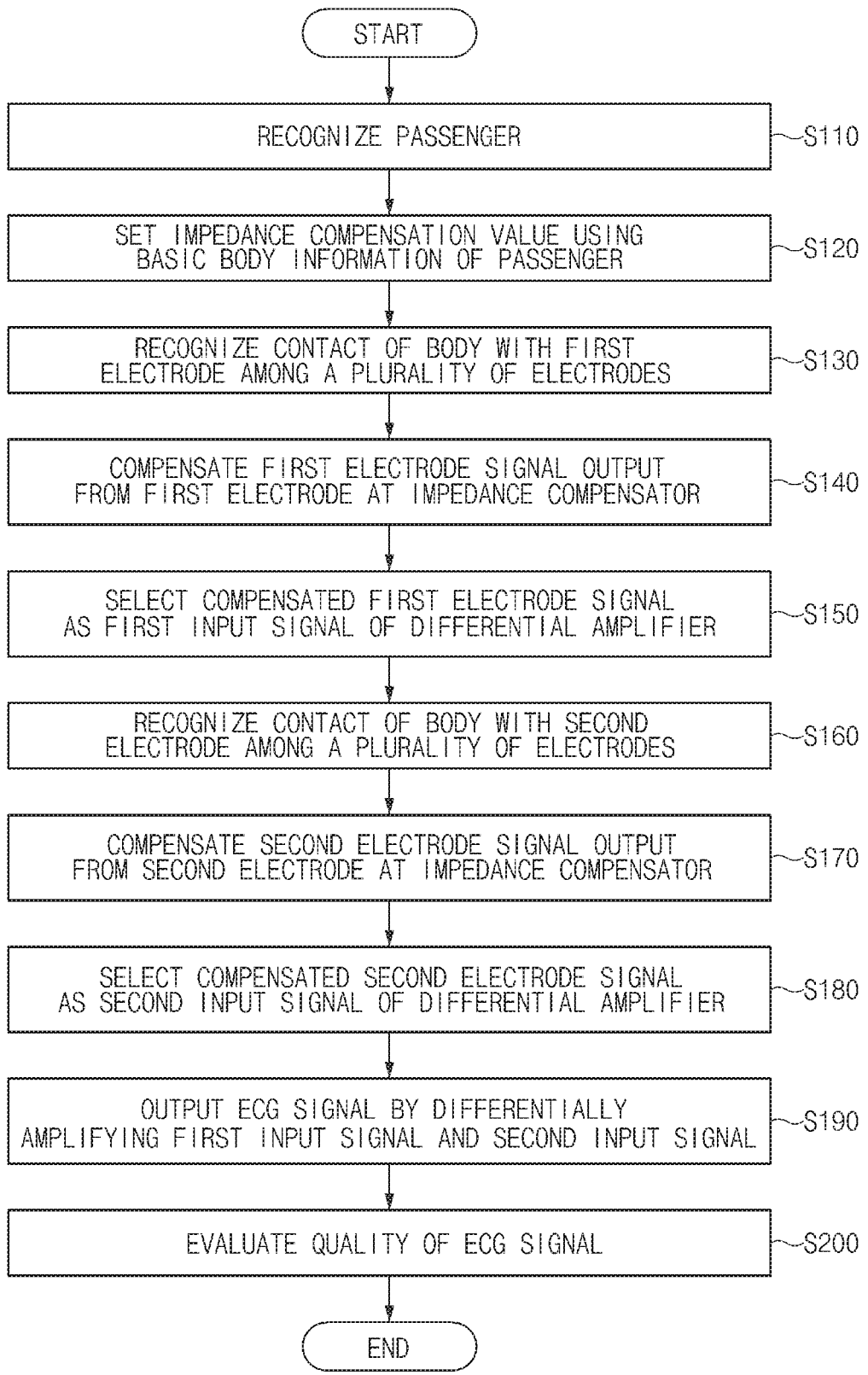
FIG. 4 is an exemplary flowchart illustrating an ECG measurement method in a vehicle according to an exemplary embodiment of the present disclosure.

Hereinafter, referring to FIG. 4, a description will be given of an ECG measurement method in a vehicle according to an exemplary embodiment of the present disclosure. FIG. 4 is an exemplary flowchart illustrating an ECG measurement method in a vehicle according to an exemplary embodiment of the present disclosure. Referring to FIG. 4, during operation S110, an ECG measurement device 100 for a vehicle of FIG. 1 may be configured to recognize a driver within the vehicle. In operation S120, the ECG measurement device 100 may be configured to determine an impedance compensation value using basic body information of the driver.

When recognizing contact of a body of the driver with a first electrode among a plurality of electrodes in operation S130, in operation S140, the ECG measurement device 100 may be configured to compensate impedance of a first electrode signal output from the first electrode at the impedance compensator using a predetermined impedance compensation value. When selecting the compensated first electrode signal as a first input signal of a differential amplifier 160 of FIG. 1 in operation S150 and when recognizing contact of a body of the driver with a second electrode among the plurality of electrodes in operation S160, in operation S170, the ECG measurement device 100 may be configured to compensate an impedance of a second electrode signal output from the second electrode using a predetermined impedance compensation value. In operation S180, the ECG measurement device 100 may be configured to select the compensated second electrode signal as a second input signal of the differential amplifier 160. In operation S190, the differential amplifier 160 may be configured to differentially amplify the first input signal and the second input signal to output an ECG signal.

In operation S200, the ECG measurement device 100 may be configured to evaluate the quality of the ECG signal. For example, if when a hand of the driver is in contact with electrode 3, an impedance of electrode signal 3 output from electrode 3 may be compensated using predetermined impedance compensation value 3, and the compensated electrode signal 3 may be transmitted to an electrode selector. When a hand of the driver is in contact with electrode 6, an impedance of electrode signal 6 output from electrode 6 may be configured to be compensated using predetermined impedance compensation value 6, and the compensated electrode signal 6 may be transmitted to the electrode selector. The electrode selector may be configured to select the compensated electrode signal 3 as a first input signal and may be configured to select the compensated electrode signal 6 as a second input signal. Accordingly, the first input signal and the second input signal may be transmitted to a differential amplifier. Thereafter, when quality deteriorates as a result of evaluating the quality of an ECG signal output from the differential amplifier at a signal quality evaluator, a compensation controller may be configured to perform the impedance compensation of the ECG signal.

Figure 5:
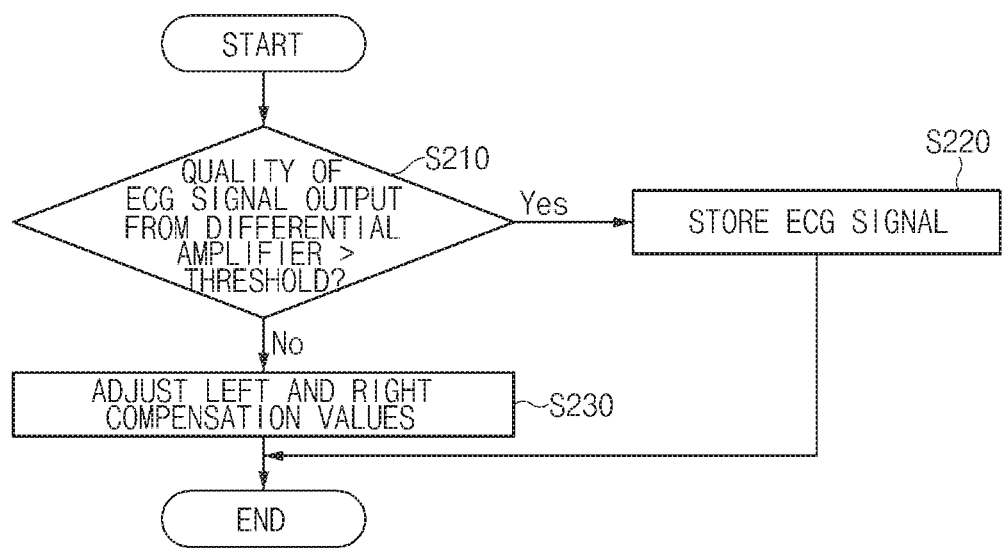
FIG. 5 is an exemplary flowchart illustrating a method for measuring quality of an ECG signal according to an exemplary embodiment of the present disclosure.

Hereinafter, a description will be given of a method for measuring quality of an ECG signal according to an exemplary embodiment of the present disclosure with reference to FIG. 5. FIG. 5 is an exemplary flowchart illustrating a method for measuring quality of an ECG signal according to an exemplary embodiment of the present disclosure.

First, in operation S210, an ECG measurement device 100 for a vehicle shown in FIG. 1 may be configured to determine whether quality of an ECG signal output from a differential amplifier 160 of FIG. 1 is greater than or equal to a threshold. When the quality of the ECG signal is greater than or equal to the threshold, in operation S220, the ECG measurement device 100 may be configured to store the ECG signal. When the quality of the ECG signal is less than the threshold, in operation S230, the ECG measurement device 100 may be configured to adjust an impedance compensation value for each of a first electrode signal (e.g., a first hand) and a second electrode signal (e.g., a second hand). In particular, although impedance differs for each user, since left and right hands of a user are similar to each other, the ECG measurement device 100 may be configured to adjust the impedance compensation value for the first electrode signal (and may be configured to adjust the impedance compensation value for the second electrode signal to the impedance compensation value for the first electrode signal.

Generally, two signals for supplying alternating current (AC) may be additionally in contact with the user when a common mode noise is removed by measuring impedance after AC flows within the driver's body, measuring a level of a common mode noise, and adjusting an amplification rate of an input signal. In an exemplary embodiment of the present disclosure, an AC signal output and an additional contact point for the AC signal output may be unnecessary. Further, an exemplary embodiment of the present disclosure may be configured to compensate an impedance of an N channel in multiple channels for overcoming shortcomings of a 2-channel common mode rejection ratio (CMRR).

An exemplary embodiment of the present disclosure may be configured to maintain measurement of a high-quality ECG by applying an impedance compensation circuit according to an electrode based on multiple electrodes and preventing deterioration in ECG measurement quality based on a selected electrode. In particular, when a first arm (e.g., left arm) of a driver is positioned at a window in a vehicle environment and a second arm (e.g., right arm) is positioned on a middle place of a vehicle in the vehicle environment, biometric features of the driver's body, input from both hands, may often differ from each other by an environment (the driver's first body part is increased in body temperature and is decreased in an amount of body water by external light, whereas the driver's second body part is relatively decreased in body temperature and is increased in an amount of body water). Thus, although a noise generated by the vehicle is not introduced, quality of an ECG signal may deteriorate. An exemplary embodiment of the present disclosure may obtain a high-quality ECG signal by adjusting environment imbalance OF both measurement devices.

Further, an exemplary embodiment of the present disclosure may provide an interface convenient for use by providing various measurement scenarios to a user in a vehicle environment through ECG measurement based on multiple electrodes. Typically, when an external noise is introduced, a high-quality signal may be obtained using a common mode rejection characteristic of a differential amplifier. However, when phases and levels of a noise input from a plurality of sides differ from each other and a noise removed by the common mode rejection characteristic is degraded, a high-quality signal may not be obtained. However, an exemplary embodiment of the present disclosure may recognize diminished signal quality when a noise is high and may be configured to adjust balance of a plurality of input signals to correct a different phase or level as a similar level and measure a high-quality signal.

Further, an exemplary embodiment of the present disclosure may obtain a high-quality signal within a quick time by recognizing a particular driver and adjusting a default setting of impedance to a predetermined value of the driver. For example, an exemplary embodiment of the present disclosure may be configured to apply a correction value reflected after an environment in a vehicle and an external environment are combined with each other. Further, when a destination is determined in a navigation device, although a driver starts and turns off the vehicle in a middle point, when there is a high probability that the driver will be the same driver, an exemplary embodiment of the present disclosure may be configured to determine a value in which a previous setting is maintained to a default value to rapidly adjust to the proper setting.

Further, when a driver operates the vehicle in a specific place using global positioning system (GPS) information, an exemplary embodiment of the present disclosure may determine whether the driver's body state is changed. When there is a specific fact, an exemplary embodiment of the present disclosure may be configured to store corresponding place information and unusual information and may use the stored information to correct an ECG signal when the driver operates a vehicle in the same place to obtain a high-quality signal.

Further, an exemplary embodiment of the present disclosure may be configured to facilitate personalized adaptive impedance tracking by determining a change in a body of a user according to an environment in a vehicle per user, predicting a change in the driver's body in a specific environment and adjusting a compensation circuit. Further, an exemplary embodiment of the present disclosure may be configured to determine a unique noise component generated in the vehicle itself based on a driving mode (e.g., an eco-mode, a sport mode, or the like) and may be configured to obtain a high-quality signal using a method for removing a noise in a corresponding frequency or enhancing attenuation of a corresponding frequency at an impedance compensator.

Figure 10:
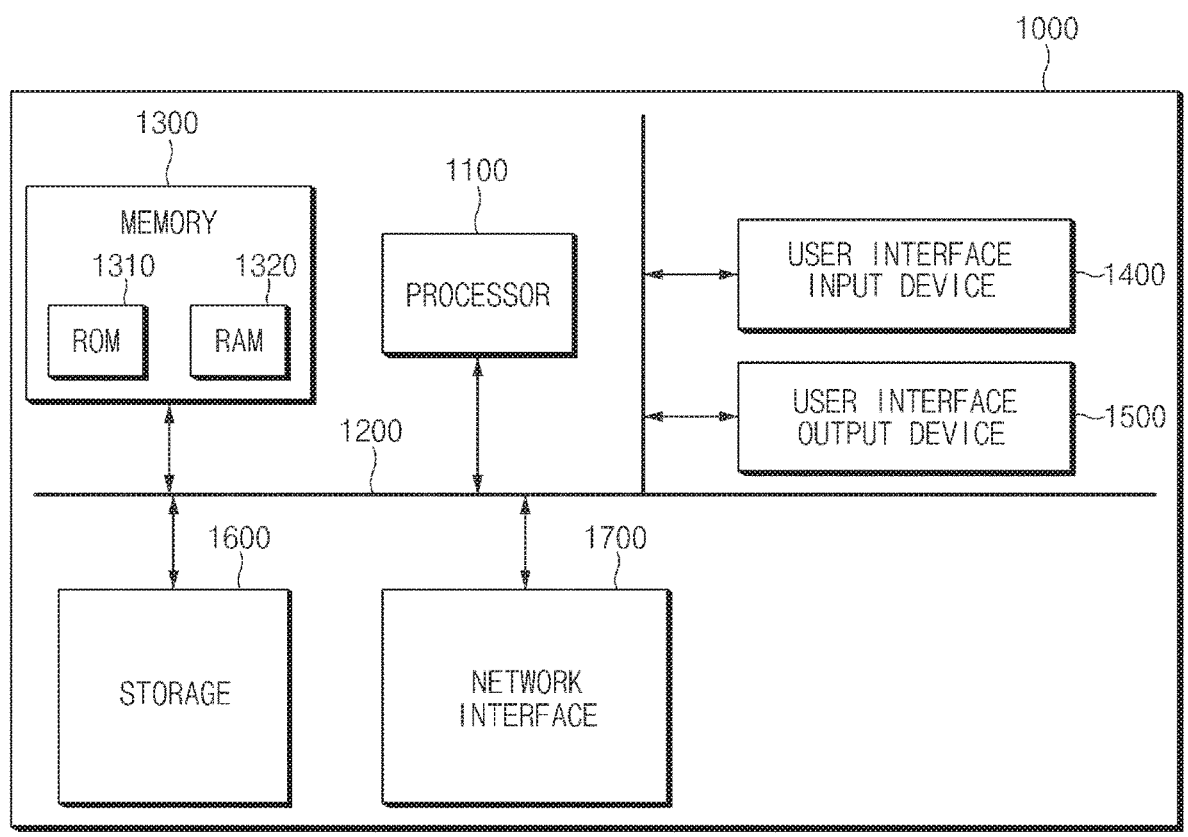
FIG. 10 is an exemplary block diagram illustrating a configuration of a computer system to which an ECG measurement method for a vehicle is applied, according to an exemplary embodiment of the present disclosure.

FIG. 10 is an exemplary block diagram illustrating a configuration of a computer system to which an ECG measurement method for a vehicle is applied, according to an exemplary embodiment of the present disclosure. Referring to FIG. 10, a computing system 1000 may include a (e.g., at least one) processor 1100, a memory 1300, a driver interface input device 1400, a driver interface output device 1500, a storage 1600, and a network interface 1700, which are connected with each other via a bus 1200. The processor 1100 may be a central processing unit (CPU) or a semiconductor device configured to process instructions stored in the memory 1300 and/or the storage 1600. Each of the memory 1300 and the storage 1600 may include various types of volatile or non-volatile storage media. For example, the memory 1300 may include a read only memory (ROM) and a random access memory (RAM).

Thus, the operations of the methods or algorithms described in connection with the exemplary embodiments disclosed in the specification may be directly implemented with a hardware module, a software module, or two combinations thereof, executed by the processor 1100. The software module may reside on a storage medium (e.g., the memory 1300 and/or the storage 1600) such as a RAM, a flash memory, a ROM, an erasable and programmable ROM (EPROM), an electrically EPROM (EEPROM), a register, a hard disc, a removable disc, or a compact disc-ROM (CD-ROM). An exemplary storage medium may be coupled to the processor 1100. The processor 1100 may be configured to output (e.g., read out) information from the storage medium and may be configured to write information in the storage medium. Alternatively, the storage medium may be integrated with the processor 1100. The integrated processor and storage medium may reside in an application specific integrated circuit (ASIC). The ASIC may reside in a driver's terminal. Alternatively, the integrated processor and storage medium may reside as a separate component of the driver terminal. The present technology may more accurately measure an ECG in various situations of a driver based on a plurality of multiple electrodes while a vehicle is driven.

While the present disclosure has been described with reference to exemplary embodiments, it will be apparent to those skilled in the art that various changes and modifications may be made without departing from the spirit and scope of the present disclosure. Therefore, exemplary embodiments of the present disclosure are not limiting, but illustrative, and the spirit and scope of the present disclosure is not limited thereto.

What is claimed is:

1. An electrocardiogram (ECG) measurement device for a vehicle, comprising:
    a plurality of electrodes configured to measure potential difference between two portions of a body of a driver;
    a plurality of impedance compensators respectively connected to the plurality of electrodes and configured to compensate an impedance of each of a plurality of electrode signals received from the plurality of electrodes, respectively;
    an electrode selector configured to sequentially select a first electrode signal and a second electrode signal of the plurality of electrode signals compensated by the plurality of impedance compensators;
    a differential amplifier configured to receive the first electrode signal and the second electrode signal as inputs, differentially amplify the first and second electrode signals, and output a differentially amplified result of the first and second electrode signals as an ECG signal;
    a signal quality evaluator configured to evaluate quality of the ECG signal output from the differential amplifier; and
    a compensation controller configured to further adjust the impedance compensation values of each of the plurality of electrode signals received from the plurality of impedance compensators if the quality of the ECG signal is less than a predetermined threshold.

2. The device of claim 1, wherein the signal quality evaluator is configured to:
    detect strength and a noise component of the ECG signal; and
    evaluate the quality of the ECG signal based on the detected strength and noise component of the ECG signal.

3. The device of claim 2, wherein at least one of the plurality of electrodes is disposed in one selected from the group consisting of: a steering wheel, a gear change lever, a window button, a door armrest, a radio volume adjuster, an armrest, a handle, a horn, a turn signal level, a glove compartment, and a seat belt.

4. The device of claim 1, further comprising:
    a contact sensor configured to detect that the body of the driver is in contact with at least one of the plurality of electrodes and configured to transmit active signals to the impedance compensator, when the body of the driver is in contact with the at least one of the plurality of electrodes.

5. The device of claim 1, wherein the compensation controller is configured to:
    adjust an impedance compensation value of the first electrode signal of the differential amplifier among the impedance compensation values of each of the plurality of electrode signals or an impedance compensation value of the second electrode signal of the differential amplifier among the impedance compensation values of each of the plurality of electrode signals on an independent basis as a result of evaluating the quality of the ECG signal.

6. The device of claim 1, wherein the compensation controller is configured to:
  terminate the adjustment of the impedance compensation values when the quality of the ECG signal is greater than the predetermined threshold.

7. An electrocardiogram (ECG) measurement system for a vehicle, comprising:
  an ECG measurement device for the vehicle, comprising:
    a plurality of electrodes configured to measure potential difference between two portions of a body of a driver;
    a plurality of impedance compensators respectively connected to the plurality of electrodes and configured to compensate an impedance of each of a plurality of electrode signals received from the plurality of electrodes, respectively;
    an electrode selector configured to sequentially select a first electrode signal and a second electrode signal of the plurality of electrode signals compensated by the plurality of impedance compensators;
    a differential amplifier configured to receive the first electrode signal and the second electrode signal as inputs, differentially amplify the first and second electrode signals, and output a differentially amplified result of the first and second electrode signals as an ECG signal;
    a signal quality evaluator configured to evaluate quality of the ECG signal output from the differential amplifier; and
    a compensation controller configured to further adjust the impedance compensation values of each of the plurality of electrode signals received from the plurality of impedance compensators if the quality of the ECG signal is less than a predetermined threshold; and
    an ECG recorder configured to store the ECG signal and the result of evaluating the quality of the ECG signal.

8. The system of claim 7, wherein the signal quality evaluator is configured to detect strength and a noise component of the ECG signal output from the differential amplifier, and evaluate the quality of the ECG signal based on the detected strength and noise component of the ECG signal.

9. The system of claim 7, wherein at least one of the plurality of electrodes is disposed in one selected from the group consisting of: a steering wheel, a gear change lever, a window button, a door armrest, a radio volume adjuster, an armrest, a handle, a horn, a turn signal level, a glove compartment, and a seat belt.

10. The system of claim 7, wherein the ECG measurement device for the vehicle further comprises:
  a contact sensor configured to detect that the body of the driver is in contact with at least one of the plurality of electrodes and transmit active signals to the impedance compensator, when the body of the driver is in contact with the at least one of the plurality of electrodes.

11. The system of claim 7, further comprising an interface configured to display the ECG signal output from the differential amplifier.

* * * * *